United States Patent
Govari et al.

(10) Patent No.: US 12,114,918 B2
(45) Date of Patent: *Oct. 15, 2024

(54) DYNAMIC ABLATION AND SENSING ACCORDING TO CONTACT OF SEGMENTED ELECTRODES

(71) Applicant: BIOSENSE WEBSTER (ISRAEL) LTD., Yokneam (IL)

(72) Inventors: Assaf Govari, Haifa (IL); Andres Claudio Altmann, Haifa (IL); Israel Zilberman, Yokneam (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 140 days.

This patent is subject to a terminal disclaimer.

(21) Appl. No.: 16/541,374

(22) Filed: Aug. 15, 2019

(65) Prior Publication Data

US 2021/0045805 A1 Feb. 18, 2021

(51) Int. Cl.
*A61B 18/14* (2006.01)
*A61B 5/00* (2006.01)
(Continued)

(52) U.S. Cl.
CPC .......... *A61B 18/1492* (2013.01); *A61B 5/287* (2021.01); *A61B 5/6853* (2013.01);
(Continued)

(58) Field of Classification Search
CPC ................ A61B 18/1492; A61B 5/287; A61B 5/6858; A61B 5/6854; A61B 5/6855;
(Continued)

(56) References Cited

U.S. PATENT DOCUMENTS

| 5,391,199 A | 2/1995 | Ben Haim |
| 5,496,312 A | 3/1996 | Klicek |

(Continued)

FOREIGN PATENT DOCUMENTS

| RU | 2608619 C2 | 1/2017 |
| RU | 2655294 C2 | 5/2018 |

(Continued)

OTHER PUBLICATIONS

U.S. Appl. No. 15/991,291, filed May 29, 2018, entitled "Touch Detection by Different Frequency Response of Tissue".

(Continued)

*Primary Examiner* — Linda C Dvorak
*Assistant Examiner* — Lindsay Regan Lancaster
(74) *Attorney, Agent, or Firm* — Dergosits & Noah LLP; Todd A. Noah

(57) ABSTRACT

A system includes an expandable distal end of a catheter and a processor. The expandable distal end has multiple electrodes that are configured to be placed in contact with a tissue in an organ and to apply ablative power to tissue. The processor is configured to, during application of the ablative power, determine whether a physical contact between the electrodes and tissue meets a predefined contact quality, and, if the physical contact of an electrode among the electrodes with the tissue does not meet the predefined contact quality, re-use the electrode for electrophysiological (EP) sensing.

20 Claims, 3 Drawing Sheets

(51) Int. Cl.
*A61B 5/287* (2021.01)
*A61B 18/00* (2006.01)

(52) U.S. Cl.
CPC .......... *A61B 5/6858* (2013.01); *A61B 5/6885* (2013.01); *A61B 2018/00029* (2013.01); *A61B 2018/0022* (2013.01); *A61B 2018/00267* (2013.01); *A61B 2018/00375* (2013.01); *A61B 2018/00386* (2013.01); *A61B 2018/00577* (2013.01); *A61B 2018/00613* (2013.01); *A61B 2018/00821* (2013.01); *A61B 2018/00839* (2013.01); *A61B 2018/00845* (2013.01); *A61B 2018/00875* (2013.01); *A61B 2018/00958* (2013.01)

(58) Field of Classification Search
CPC ............. A61B 2018/00029; A61B 2018/0022; A61B 2018/00267; A61B 2018/00577; A61B 5/6853; A61B 5/6885; A61B 2018/00375; A61B 2018/00386; A61B 2018/00613; A61B 2018/00821; A61B 2018/00839; A61B 2018/00845; A61B 2018/00875; A61B 2018/00958; A61B 2018/0016; A61B 2018/00654; A61B 2018/00678; A61B 2018/00797; A61B 2018/124; A61B 2034/2046; A61B 5/0536; A61B 18/00; A61B 18/12; A61B 18/1233; A61B 2018/00351; A61B 2018/00541; A61B 2018/00666; A61B 2018/00702; A61B 2018/00791; A61B 2018/142; A61B 2018/1467; A61B 18/14; A61M 25/10
See application file for complete search history.

(56) References Cited

U.S. PATENT DOCUMENTS

| | | | | |
|---|---|---|---|---|
| 5,769,847 | A * | 6/1998 | Panescu | G01K 3/14 |
| | | | | 607/101 |
| 5,836,874 | A * | 11/1998 | Swanson | A61B 18/1492 |
| | | | | 606/41 |
| 5,836,990 | A * | 11/1998 | Li | A61N 1/056 |
| | | | | 607/28 |
| 6,053,912 | A | 4/2000 | Panescu | |
| 6,113,592 | A | 9/2000 | Taylor | |
| 6,183,468 | B1 | 2/2001 | Swanson | |
| 6,239,724 | B1 | 5/2001 | Doron | |
| 6,241,724 | B1 * | 6/2001 | Fleischman | A61N 1/0565 |
| | | | | 606/41 |
| 6,332,089 | B1 | 12/2001 | Acker | |
| 6,391,024 | B1 | 5/2002 | Sun et al. | |
| 6,484,118 | B1 | 11/2002 | Govari | |
| 6,618,612 | B1 | 9/2003 | Acker | |
| 6,690,963 | B2 | 2/2004 | Ben Haim | |
| 7,756,576 | B2 | 7/2010 | Levin | |
| 7,848,787 | B2 | 12/2010 | Osadchy | |
| 7,869,865 | B2 | 1/2011 | Govari | |
| 8,456,182 | B2 | 6/2013 | Bar-Tal | |
| 8,668,686 | B2 | 3/2014 | Govari et al. | |
| 2002/0065455 | A1 | 5/2002 | Ben Haim | |
| 2003/0120150 | A1 | 6/2003 | Govari | |
| 2004/0068178 | A1 | 4/2004 | Govari | |
| 2008/0288038 | A1 | 11/2008 | Paul et al. | |
| 2008/0312521 | A1 | 12/2008 | Solomon | |
| 2012/0071772 | A1 | 3/2012 | Chetham | |
| 2012/0136348 | A1 * | 5/2012 | Condie | A61B 18/14 |
| | | | | 606/34 |
| 2013/0072774 | A1 | 3/2013 | Greenspan | |
| 2013/0123778 | A1 * | 5/2013 | Richardson | A61B 18/1492 |
| | | | | 606/41 |
| 2014/0243809 | A1 * | 8/2014 | Gelfand | A61B 18/16 |
| | | | | 606/28 |
| 2015/0141978 | A1 | 5/2015 | Subramaniam | |
| 2015/0272470 | A1 | 10/2015 | Slizynski et al. | |
| 2016/0242667 | A1 | 8/2016 | Fay et al. | |
| 2016/0278841 | A1 | 9/2016 | Panescu et al. | |
| 2016/0287136 | A1 | 10/2016 | Condie et al. | |
| 2016/0287137 | A1 | 10/2016 | Condie et al. | |
| 2017/0156791 | A1 * | 6/2017 | Govari | A61B 5/287 |
| 2018/0078170 | A1 | 3/2018 | Panescu | |
| 2018/0078300 | A1 | 3/2018 | Paul et al. | |
| 2019/0104933 | A1 * | 4/2019 | Stern | A61B 1/307 |
| 2020/0015876 | A1 | 1/2020 | Chou et al. | |

FOREIGN PATENT DOCUMENTS

| | | |
|---|---|---|
| WO | WO1996005768 A1 | 2/1996 |
| WO | WO2014008489 A1 | 1/2014 |
| WO | WO2016090175 A1 | 6/2016 |
| WO | 20160181318 A1 | 11/2016 |

OTHER PUBLICATIONS

Search Report from corresponding European Patent Application No. 20191096.5, dated Dec. 15, 2020.

Search Report from related European Patent Application No. 19177055.1, dated Oct. 18, 2019.

Hong, Cao et al., "Using Electrical Impedance to Predict Catheter-Endocardial Contact During RF Cardiac Ablation," IEEE Transactions on Biomedical Engineering, 49:3, Mar. 1, 2002.

* cited by examiner

DYNAMIC ABLATION AND SENSING ACCORDING TO CONTACT OF SEGMENTED ELECTRODES

FIELD OF THE INVENTION

The present invention relates generally to medical probes, and particularly to cardiac radiofrequency (RF) ablation and electrophysiological (EP) sensing multi-electrode catheters.

BACKGROUND OF THE INVENTION

Techniques that use a medical probe to perform temperature-monitored ablation of intra body tissue were previously proposed in the patent literature. For example, U.S. Pat. No. 6,053,912 describes systems and associated methods for ablating body tissue that employ an electrode for contacting tissue to form a tissue-electrode interface. The electrode is adapted to be connected to a source of ablation energy to conduct ablation energy for transmission by the electrode into tissue at the tissue-electrode interface. The systems and methods also include an element to cool the electrode. The systems and methods hold a tissue temperature sensing element in a carrier in thermal conductive contact with tissue beneath the tissue-electrode interface. The systems and methods include a controller that is coupled to the tissue temperature sensing element to control either the supply of ablation energy, or the rate at which the electrode is cooled, or both, based at least in part, upon temperature sensed by the temperature sensing element.

As another example, U.S. Pat. No. 5,496,312 describes a control that responds to impedance and temperature between active and return electrodes of the electrosurgical generator during tissue desiccation. Tissue contacts separately and independently provide high frequency power to effect tissue electrosurgically. A method of control responds to tissue impedance by supplying high frequency power separately and independently to contacts, monitoring, regulating and controlling impedance between the contacts and the return electrode. The method sets the generator power applied by each contact, and transmits temperature values for each contact with sensors, to regulate contact power.

SUMMARY OF THE INVENTION

The present invention provides a system including an expandable distal end of a catheter and a processor. The expandable distal end has multiple electrodes that are configured to be placed in contact with tissue in an organ and to apply ablative power to the tissue. The processor is configured to, during application of the ablative power, determine whether a physical contact between the electrodes and tissue meets a predefined contact quality, and, if the physical contact of an electrode among the electrodes with the tissue does not meet the predefined contact quality, re-use the electrode for electrophysiological (EP) sensing.

In some exemplary embodiments, the ablative power includes at least one of a radiofrequency (RF) power output by an RF generator and irreversible electroporation (IRE) pulses output by an IRE pulse generator.

In some exemplary embodiments, the system further includes a switching assembly configured to switch the electrode between a generator of the ablative power and an EP sensing system, wherein the processor is configured to control the switching assembly to (i) initially connect the electrode to the generator and (ii) subsequently connect the electrode to the EP sensing system for re-using the electrode for EP sensing.

In an exemplary embodiment, each of the electrodes includes a plurality of electrode segments, wherein the switching assembly and the processor are configured to individually switch any of the electrode segments between the generator and the EP sensing system.

In another exemplary embodiment, the system further includes a switching assembly configured to initially have each of the electrodes connected in parallel to a generator of the ablative power and to an EP sensing system, wherein the processor is configured to control the switching assembly to subsequently disconnect the electrode from the generator for re-using the electrode for EP sensing.

In still another exemplary embodiment, each of the electrodes includes a plurality of electrode segments, wherein the switching assembly and the processor are configured to individually disconnect any of the electrode segments from the generator.

In some exemplary embodiments, the processor is configured to determine whether the physical contact of the electrode meets the predefined contact quality, by evaluating a preset temperature criterion. In other exemplary embodiments, the processor is configured to evaluate the preset temperature criterion by evaluating a relation of a measured temperature of the electrode to a preset threshold temperature.

In another exemplary embodiment, the processor is configured to determine whether the physical contact of the electrode meets the predefined contact quality, by evaluating a preset impedance criterion. In another exemplary embodiment, the processor is configured to evaluate the impedance criterion by assessing whether a frequency-dependence of the impedance indicates that the electrode contacts blood or indicates that the electrode contacts tissue.

There is additionally provided, in accordance with an exemplary embodiment of the present invention, a method including placing an expandable distal end of a catheter having multiple electrodes in contact with tissue of an organ. Ablative power is applied to the multiple electrodes. During application of the ablative power, it is determined whether a physical contact between the electrodes and the tissue meets a predefined contact quality. If the physical contact of an electrode among the electrodes with the tissue does not meet the predefined contact quality, the electrode is re-used for electrophysiological (EP) sensing.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
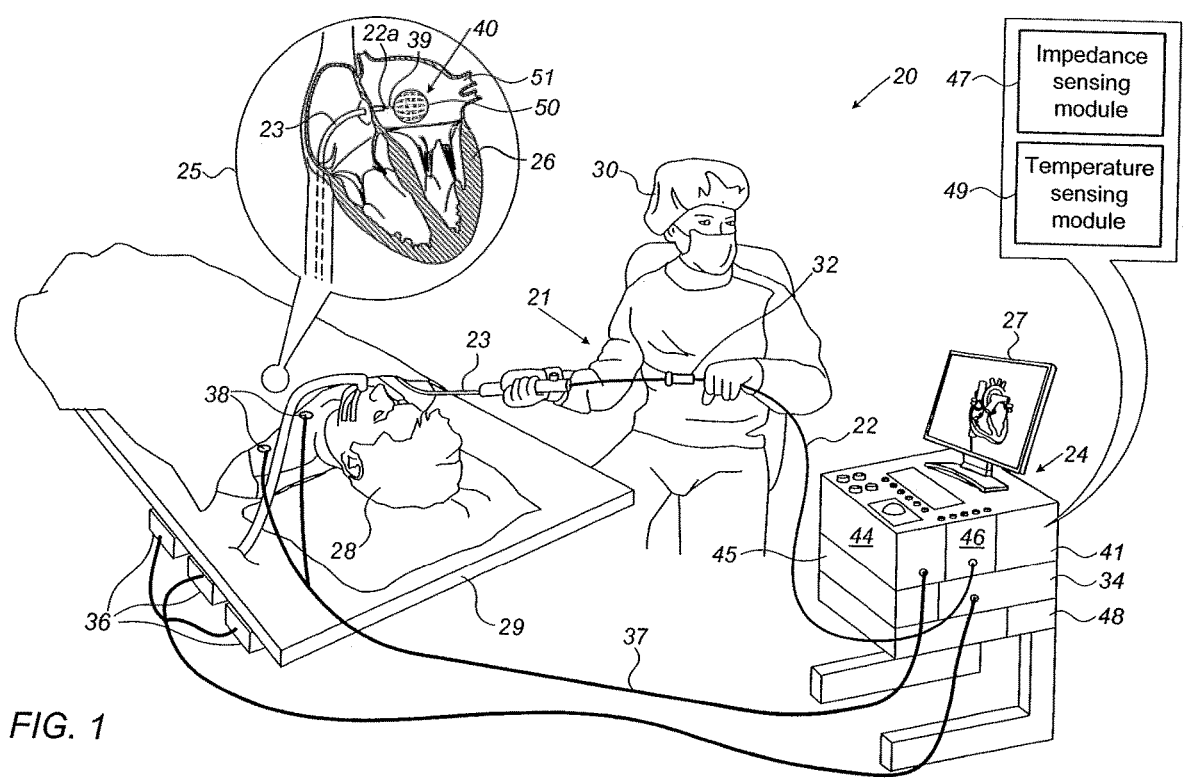
FIG. 1 is a schematic, pictorial illustration of a catheter-based, position-tracking and balloon-ablation system, in accordance with an exemplary embodiment of the present invention.

For efficient ablation with a medical probe, such as an intra-cardiac radiofrequency (RF) multi-electrode catheter and/or an irreversible electroporation (IRE) multi-electrode catheter, it is important that the ablating electrodes disposed over the catheter are in good physical contact with the tissue being ablated. For example, when a balloon catheter with multiple ablation electrodes is used to ablate tissue in an organ, such as an ostium of a pulmonary vein (PV), typically all of the catheter electrodes are positioned to contact the PV. However, the contact of some of the electrodes may not be sufficient for effective and safe ablation.

Similarly, with other multi-electrode catheters, such as the Lasso catheter (made by Biosense Webster, Irvine, California) or a basket catheter, they may also have only part of their electrodes in sufficient contact with tissue for ablation.

For these electrodes, rather than ablating tissue, an applied RF power may cause unwanted effects such as clot formation. In case of IRE, an incomplete PV isolation may occur, but without known unwanted effects.

In the context of the present patent application, the term "applying ablative power" covers both applying RF power and applying IRE pulses. Typically, the ablative power comprises either a radiofrequency (RF) power output by an RF generator or irreversible electroporation (IRE) pulses output by an IRE pulse generator. However, a single generator may be configured to interchangeably output RF power and IRE pulses.

Exemplary embodiments of the present invention that are described hereinafter provide techniques to apply ablation and electrophysiological (EP) sensing in a spatially selectable manner. In some exemplary embodiments, an expandable multi-electrode catheter (e.g., inflatable balloon catheter) is provided that comprises electrodes divided into segments (i.e., into electrode segments). Further provided is a processor-controlled switching box (also referred to as switching assembly). During application of ablative power by the electrode segments, depending on whether, and how well, an electrode segment among the electrode segments of the multi-electrode catheter contacts tissue, the processor can, by controlling the switching box, switch to re-use the electrode segment as a sensor. In another exemplary embodiment, the processor controlling the switching box can switch the electrode segment between operating as an ablation electrode and operating as a sensing electrode applied to, for example, acquiring intracardiac electrogram signals (i.e., for electrophysiological (EP) sensing).

In some exemplary embodiments, by way of example of a multi-electrode catheter, a balloon catheter is provided with ten electrodes disposed on a membrane of the balloon. Each of the ten electrodes is divided into four segments with one or more temperature sensors, such as thermocouples, located on each electrode segment. Initially the switching box connects all the segments of each electrode as ablation electrodes as the catheter is positioned in contact with an ostium, and RF ablative power is supplied to the electrodes. During application of ablative power to an electrode segment, the one or more temperature sensors sense the rising temperature of the electrode segment in real-time.

The temperature of each electrode segment is monitored by a processor receiving temperature readings sensed by the one or more temperature sensors. The processor uses a preset temperature criterion, such as a relation of the temperature readings with respect to a preset threshold temperature, to determine sufficiency of contact (i.e., to determine whether a physical contact between any of the electrodes and tissue meets a predefined contact quality with tissue). For example, if a temperature reading from of an electrode segment is above the preset threshold temperature (e.g., a threshold determined by previous experimentation), the processor determines that the contact of the electrode segment with the tissue is good, i.e., meeting a predefined contact quality criterion, and that tissue is being ablated. In this case the switching box continues to connect the electrode segment to the ablative power source.

If, on the other hand, the temperature of an electrode segment does not rise above the threshold temperature, the processor determines that the level of contact of the electrode segment with tissue is insufficient (meaning that the ablative energy mainly heats blood). In this case the processor controls the switching box to switch the electrode segment from receiving ablation power to acting as a sensing electrode.

In an exemplary embodiment, it is sufficient that one of the one or more temperature sensors measures a temperature below or equal to the threshold temperature to switch the electrode segment into a sensing electrode. In another exemplary embodiment, the processor compares an average temperature sensed by the one or more temperature sensors to the threshold temperature, and controls the switching box according to the average electrode segment temperature.

In an alternative exemplary embodiment, the switching assembly is configured to initially have each of the electrode segments connected in parallel to a generator of the ablative power and to an EP sensing system. Upon deciding that the level of contact of a given electrode segment with tissue is insufficient, the processor is configured to control the switching assembly to disconnect the electrode segment from the generator.

In some exemplary embodiments, the ablation system is additionally, or alternatively, configured to measure an impedance between each electrode segment and tissue. A processor of the system analyzes a characteristic of the measured impedance, for example, different frequency-dependence of the impedance of blood and tissue, and, using the outcome of the analysis, provides an independent assessment for each electrode segment as to whether the electrode segment is in direct electrical contact with (i.e., touches) cardiac tissue or is not in contact (e.g., the electrode segment is mostly immersed in blood).

When using impedance measurements alone, initially the switching box has all of the electrode segments of all of the electrodes connected as sensing electrodes. The catheter is positioned in contact with tissue, such as of an ostium of a PV, and impedances are measured. Each electrode having a frequency-dependent impedance indicative of tissue connected to the ablative power source by the processor, using the switching box. An electrode segment with a frequency-dependent impedance indicative of blood is kept by the processor switched as a sensing electrode.

In some exemplary embodiments, just prior to applying RF power, the aforementioned impedance-measurement-based touch indication with tissue may be utilized, for example, to reposition the multi-electrode catheter inside the lumen to improve contact of an electrode segment determined to be mostly in contact with blood.

A technique for sensing of electrode-tissue physical contact using analysis of frequency response of tissue is described in U.S. patent application Ser. No. 15/991,291, filed May 29, 2018, entitled "Touch Detection by Different Frequency Response of Tissue," which is assigned to the assignee of the present patent application and whose disclosure is incorporated herein by reference. In an exemplary embodiment, the processor may use this method to analyze the acquired intra-cardiac signals. However, other techniques to asses level of contact with tissue that utilize electrical measurements provided by segmented electrodes may be used.

In some exemplary embodiments, electrode segment temperature and impedance are both measured and analyzed in real-time, i.e., during the application of ablative power. Using two indications to determine whether an electrode segment can be used for ablation, or used only for sensing, can enhance the clinical selectivity of the disclosed technique.

Typically, the processor is programmed in software containing a particular algorithm that enables the processor to conduct each of the processor related steps and functions outlined above.

By providing electrode segments that are switchable according to quality of contact with tissue, the disclosed segmented balloon ablation technique can provide safer and more effective balloon ablation treatments. This, in turn, may improve the clinical outcome of cardiac balloon ablation treatments, such as of pulmonary vein (PV) isolation for treatment of arrhythmia.

SYSTEM DESCRIPTION

FIG. 1 is a schematic, pictorial illustration of a catheter-based position-tracking and balloon-ablation system 20, in accordance with an exemplary embodiment of the present invention. System 20 comprises a catheter 21 that is fit at a distal end 22a of a shaft 22 of the catheter with an RF ablation expandable balloon 40 comprising segmented electrodes 50 (seen in inset 25). In the exemplary embodiment described herein, segmented electrodes 50 are used for ablating tissue of an ostium 51 of a PV in a heart 26.

The proximal end of catheter 21 is connected to a control console 24 comprising an ablative power source 45. Console 24 includes a switching box 46 (also referred to as a switching assembly) that can switch any segment of a segmented electrodes 50 between acting as an ablation electrode and acting as a sensing electrode. An ablation protocol comprising ablation parameters including preset temperature and/or impedance criterions is stored in a memory 48 of console 24.

Physician 30 inserts distal end 22a of shaft 22 through a sheath 23 into heart 26 of a patient 28 lying on a table 29. Physician 30 navigates the distal end of shaft 22 to a target location in the heart 26 by manipulating shaft 22 using a manipulator 32 near the proximal end of the catheter and/or deflection from the sheath 23. During the insertion of distal end 22a, balloon 40 is maintained in a collapsed configuration by sheath 23. By containing balloon 40 in a collapsed configuration, sheath 23 also serves to minimize vascular trauma along the way to target location.

Once distal end 22a of shaft 22 has reached the target location, physician 30 retracts sheath 23 and inflates balloon 40, and further manipulates shaft 22 to place segmented electrodes 50 disposed over a perimeter of balloon 40 in contact with ostium 51 the pulmonary vein.

Electrodes 50 are connected by wires running through shaft 22 to processor 41 controlling switching box 46 of interface circuits 44 in a console 24. To perform its functions, processor 41 includes an ablation-electrode impedance sensing module 47 and a temperature sensing module 49.

Impedance sensing module 47 receives electrical impedance signals, measured between segmented electrodes and surface electrodes 38, which are seen in the exemplified system as attached by wires running through a cable 37 to the chest of patient 28. A method for tracking the positions of electrodes 50 using the measured impedances is implemented in various medical applications, for example in the CARTO™ system, produced by Biosense-Webster (Irvine, California) and is described in detail in U.S. Pat. Nos. 7,756,576, 7,869,865, 7,848,787, and 8,456,182, whose disclosures are all incorporated herein by reference. This method is sometimes called Advanced Catheter Location (ACL). Console 24 drives a display 27, which shows the tracked position of balloon 40 inside heart 26.

As further shown in inset 25, distal end 22a comprises a magnetic position sensor 39 contained within distal end 22a just proximally to expandable balloon 40. During navigation of distal end 22a in heart 26, console 24 receives signals from magnetic sensor 39 in response to magnetic fields from external field generators 36, for example, for the purpose of measuring the position of ablation balloon 40 in the heart and, optionally, presenting the tracked position on a display 27. Magnetic field generators 36 are placed at known positions external to patient 28, e.g., below patient table 29. Console 24 also comprises a driver circuit 34, configured to drive magnetic field generators 36.

The method of position sensing using external magnetic fields is implemented in various medical applications, for example, in the CARTO™ system, produced by Biosense-Webster and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

As noted above, control console 24 comprises a processor 41, typically a general-purpose computer, with suitable front end and interface circuits 44 for receiving signals from catheter 21, as well as for applying RF energy treatment via catheter 21 in a left atrium of heart 26 and for controlling the other components of system 20. Processor 41 typically comprises software in a memory 48 of system 20, that is programmed to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 41 runs a dedicated algorithm as disclosed herein, included in FIG. 4, that enables processor 41 to perform the disclosed steps, as further described below.

Dynamic Ablation and Sensing According to Contact of Segmented Electrodes

Figure 2:
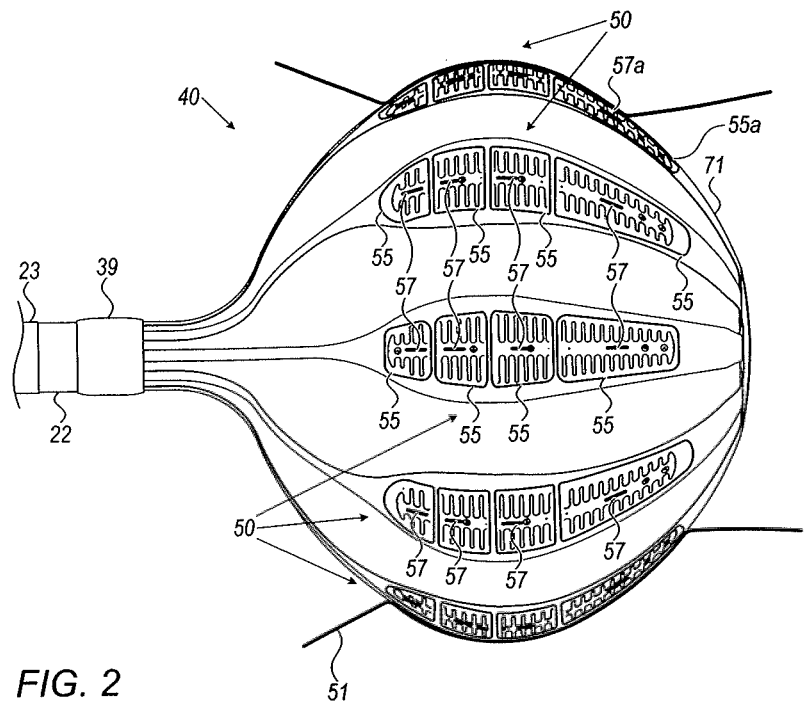
FIG. 2 is a schematic, pictorial side view of a distal end of the balloon catheter of FIG. 1 deployed in a region of a pulmonary vein (PV) and its ostium, in accordance with an exemplary embodiment of the invention.

FIG. 2 is a schematic, pictorial side view of the balloon catheter of FIG. 1 deployed in a region of a pulmonary vein (PV) and its ostium 51, in accordance with an exemplary embodiment of the invention. The balloon catheter is used to ablate ostium 51 tissue to isolate a source of arrhythmia. Balloon 40 has ten segmented electrodes 50 disposed over a membrane 71 of the balloon. RF power can be delivered from ablative power source 45 independently to each of the four electrode segments 55 of each of the ten electrodes 50, depending on the level of physical contact of each segment 55 with tissue during ablation.

Each of electrode segments 55 is fitted with a temperature sensor 57 in order to monitor electrode segment 55 temperature during ablation. While FIG. 2 shows a single temperature sensor 57 per electrode segment 55, in general, several temperature sensors 57 are disposed over each electrode segment 55. The lowest temperature reading, or the average temperature reading, may be used per electrode segment to determine quality of physical contact of segment 55 with tissue.

As seen in FIG. 2, an electrode segment 55a is not in good contact with tissue. Based on temperature readings from sensor 57a as below or equal to the preset threshold temperature during ablation, processor 41 determines the insufficient physical contact of electrode segment 55a. Responsively, processor 41 controls switching box 46 to switch electrode segment 55a into a sensing electrode.

In an alternative exemplary embodiment, switching box 46 initially connects all electrode segments 55 of all electrodes 50, in parallel, to ablative power source 45 and to the EP sensing system. Upon deciding that the level of contact of a given electrode segment 55 with tissue is insufficient, processor 41 controls switching box 46 to disconnect the electrode segment from the generator, and in this manner facilitate the re-use of this electrode segment for EP sensing.

The pictorial side view shown in FIG. 2 is chosen by way of example, where other embodiments are possible. For example, in another exemplary embodiment, cooling fluid sprays via irrigation holes (not shown) in electrodes 50 to cool ablated tissue. While FIG. 2 describes a multi-electrode balloon catheter, the principles of the disclosed techniques apply to any catheter having a distal end fitted with multiple electrodes, such as the aforementioned Lasso and basket catheters.

Figure 3:
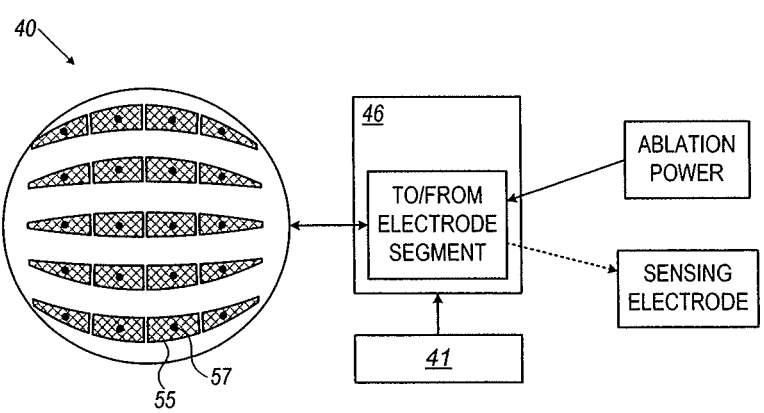
FIG. 3 is a block diagram that schematically describes the functionality of the processor-controlled switching box of FIG. 1, in accordance with an exemplary embodiment of the invention.

FIG. 3 is a block diagram that schematically describes the functionality of processor-controlled switching box 46 of FIG. 1, in accordance with an exemplary embodiment of the invention. As seen, in response to a command by processor 41, switching box 46 either connects an electrode segment to ablation power, or connects the electrode segment as a sensing electrode. For example, switching box 46 connects an electrode segment to a position sensing sub-system of system 20 to provide signal positions to be used with the aforementioned ACL position tracking method.

The block diagram of FIG. 3 is highly simplified to maintain clarity of presentation. System elements that do not contribute directly to the clarity presentation are thus omitted.

Figure 4:
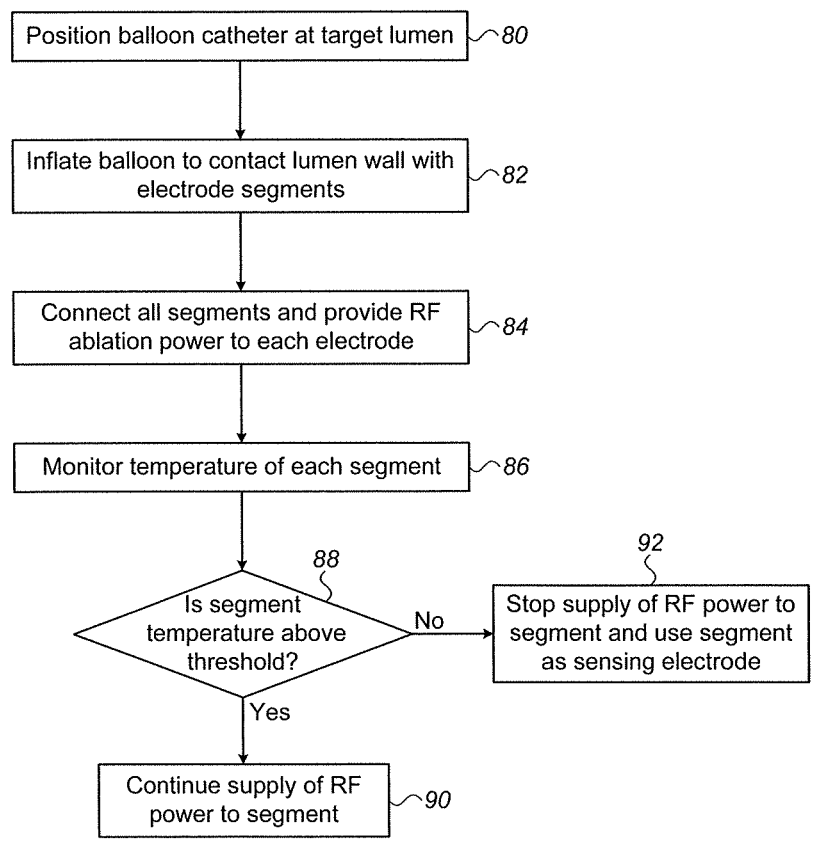
FIG. 4 is a flow chart that schematically illustrates a method for interchangeably using segmented electrodes of the balloon catheter of FIG. 2 for sensing and ablation, in accordance with an exemplary embodiment of the invention.

FIG. 4 is a flow chart that schematically illustrates a method for interchangeably using segmented electrodes of the balloon catheter of FIG. 2 for sensing and ablation, in accordance with an exemplary embodiment of the invention. The algorithm, according to the presented exemplary embodiment, carries out a process that begins when physician 30 positions the balloon catheter at a target location within a lumen of a patient, such as at ostium 51, at a balloon catheter positioning step 80. Next, physician 30 inflates balloon 40 to contact the lumen wall with electrode segments 55 over an entire circumference of the lumen, at a balloon inflation step 82.

Next, physician 30 connects all segments 55 of an electrode 50 and provides RF ablation power to each electrode 50, at an ablation step 84. At a subsequent temperature monitoring step 86, processor 41 uses measurements from one or more temperature sensors 57 to monitor a resulting temperature of each electrode segment 55. Processor 41 compares temperature readings from sensor 57 on each segment with a preset threshold temperature, at a segment temperature checking step 88.

If the segment temperature is above the preset threshold, meaning that the electrode segment is in good contact with ablated tissue, the processor controls switching box 46 to maintain the segment operation as an ablation electrode, at an ablation continuation step 90. If, on the other hand, segment temperature is below or equals the preset temperature threshold, processor 41 controls switching box 46 to stop supplying RF power to the segment and to switch the segment to operate as a sensing electrode, at a switching step 92.

The exemplary flow chart shown in FIG. 4 is chosen purely for the sake of conceptual clarity. In alternative embodiments, additional steps may be performed, such as processor 41 monitoring measured impedances of segments, and acting according to measured impedances, as described above. While FIG. 4 describes the method using multi-electrode balloon catheter, the principles of the present disclosure apply to any catheter having a distal end fitted with multiple electrodes, such as the aforementioned Lasso and basket catheters.

Although the embodiments described herein mainly address pulmonary vein isolation, the methods and systems described herein can also be used in other applications that require a determination of occlusion, such as, for example, in renal denervation, and generally, in ablating other organs.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:
1. A system, comprising:
an expandable distal end of a catheter having multiple electrodes that are configured to be placed in contact with tissue in an organ and to apply ablative power to tissue, each of the multiple electrodes comprising a plurality of electrode segments; and
a processor designed to apply ablative power and electrophysiological sensing simultaneously in a spatially selectable manner to each of the plurality of electrode segments, respectively, which is configured to:
during application of the ablative power, determine whether a physical contact between at least one of the plurality of electrode segments of one of the multiple electrodes and tissue meets a predefined contact quality, wherein physical contact is determined by at least one of evaluating temperature, impedance or temperature and impedance; and
if the physical contact of the at least one of the plurality of electrode segments does not meet the predefined contact quality, the processor causes the particular electrode segment to being switched from receiving ablative power to being re-used for electrophysiological (EP) sensing while the other electrode segments are simultaneously being utilized for ablation.

2. The system according to claim 1, wherein the ablative power comprises at least one of a radiofrequency (RF) power outputted by an RF generator and irreversible electroporation (IRE) pulses outputted by an IRE pulse generator.

3. The system according to claim 1, and comprising a switching assembly configured to switch at least one of the plurality of electrode segments between a generator of the ablative power and an EP sensing system, wherein the processor is configured to control the switching assembly to (i) initially connect the at least one electrode segment to the generator and (ii) subsequently connect the at least one electrode segment to the EP sensing system for re-using the at least one electrode segment for EP sensing.

4. The system according to claim 3, wherein the switching assembly and the processor are configured to individually switch any of the electrode segments between the generator and the EP sensing system.

5. The system according to claim 1, further comprising a switching assembly configured to initially have each of the plurality of electrode segments connected in parallel to a generator of the ablative power and to an EP sensing system, wherein the processor is configured to control the switching assembly to subsequently disconnect each of the plurality of electrode segments from the generator for re-using the particular electrode segment for EP sensing.

6. The system according to claim 5, wherein the switching assembly and the processor are configured to individually disconnect any of the electrode segments from the generator.

7. The system according to claim 1, wherein the processor is configured to determine whether the physical contact of the at least one of the plurality of electrode segments meets the predefined contact quality, by evaluating a preset temperature criterion.

8. The system according to claim 7, wherein the processor is configured to evaluate the preset temperature criterion by evaluating a relation of a measured temperature of the electrode to a preset threshold temperature.

9. The system according to claim 1, wherein the processor is configured to determine whether the physical contact of the electrode meets the predefined contact quality, by evaluating a preset impedance criterion.

10. The system according to claim 9, wherein the processor is configured to evaluate the impedance criterion by assessing whether a frequency-dependence of the impedance indicates that at least one of the plurality of electrode segments contacts blood or indicates that the electrode contacts tissue.

11. A method, comprising:
placing an expandable distal end of a catheter having multiple electrodes in contact with tissue of an organ, each of the multiple electrodes comprising a plurality of electrode segments;
applying ablative power to the multiple electrodes under processor control, the processor designed to apply ablative power and electrophysiological sensing simultaneously in a spatially selectable manner to each of the plurality of electrode segments, respectively;
during application of the ablative power, determining whether a physical contact between at least one of the plurality of electrode segments of one of the multiple electrodes and tissue meets a predefined contact quality, wherein physical contact is determined by at least one of evaluating temperature, impedance or temperature and impedance; and
if the physical contact of the at least one of the plurality of electrode segments does not meet the predefined contact quality, the processor causes the particular electrode segment to being switched from receiving ablative power to being re-used for electrophysiological (EP) sensing while the other electrode segments are simultaneously being utilized for ablation.

12. The method according to claim 11, wherein applying the ablative power comprises applying at least one of radiofrequency (RF) ablative power and applying irreversible electroporation (IRE) pulses.

13. The method according to claim 11, further comprising, using a switching assembly, switching at least one of the plurality of electrode segments between a generator of the ablative power and an EP sensing system, and controlling the switching assembly to (i) initially connect the at least one electrode segment to the generator and (ii) subsequently connect the at least one electrode segment to the EP sensing system for re-using the at least one electrode segment for EP sensing.

14. The method according to claim 13, wherein controlling the switching assembly comprises individually switching any of the electrode segments between the generator and the EP sensing system.

15. The method according to claim 11, and comprising using a switching assembly, having initially each of the plurality of electrode segments connected in parallel to a generator of the ablative power and to an EP sensing system, and controlling the switching assembly to subsequently disconnect each of the plurality of electrode segments from the generator for re-using the particular electrode segment for EP sensing.

16. The system according to claim 15, wherein controlling the switching assembly comprises individually disconnecting any of the electrode segments from the generator.

17. The method according to claim 11, wherein determining whether the physical contact of the at least one of the plurality of electrode segments meets the predefined contact quality comprises evaluating a preset temperature criterion.

18. The method according to claim 17, wherein evaluating the preset temperature criterion comprises evaluating a relation of a measured temperature of the electrode to a preset threshold temperature.

19. The method according to claim 11, wherein determining whether the physical contact of the electrode meets the predefined contact quality comprises evaluating a preset impedance criterion.

20. The method according to claim 19, evaluating the preset impedance comprises assessing whether a frequency-dependence of the impedance indicates that at least one of the plurality of electrode segments contacts blood or indicates that the electrode contacts tissue.

* * * * *